United States Patent [19]

Pfeiler

[11] 4,417,354
[45] Nov. 22, 1983

[54] DIAGNOSTIC RADIOLOGY INSTALLATION

[75] Inventor: Manfred Pfeiler, Erlangen, Fed. Rep. of Germany

[73] Assignee: Siemens Aktiengesellschaft, Berlin & Munich, Fed. Rep. of Germany

[21] Appl. No.: 251,056

[22] Filed: Apr. 6, 1981

[30] Foreign Application Priority Data

May 7, 1980 [DE] Fed. Rep. of Germany ....... 3017494

[51] Int. Cl.³ ............................................. G03B 41/16
[52] U.S. Cl. .......................................... 378/19; 378/4
[58] Field of Search ........................................ 378/19

[56] References Cited

U.S. PATENT DOCUMENTS 4,196,352  4/1980  Berninger ............................ 378/19

*Primary Examiner*—Craig E. Church
*Attorney, Agent, or Firm*—Hill, Van Santen, Steadman & Simpson

[57] ABSTRACT

An exemplary embodiment includes a patient support, a radiation measuring arrangement comprised of a radiation source which generates a fan-shaped radiation beam penetrating the radiography subject and disposed transversely to the patient support, and a radiation receiver having an array of detectors. A predetermined body region is scanned by the measuring arrangement, and, via a measurand processing circuit, an image of the scanned body region is formed. The radiation receiver is pivotally mounted about an axis disposed perpendicularly to the radiation beam.

5 Claims, 4 Drawing Figures

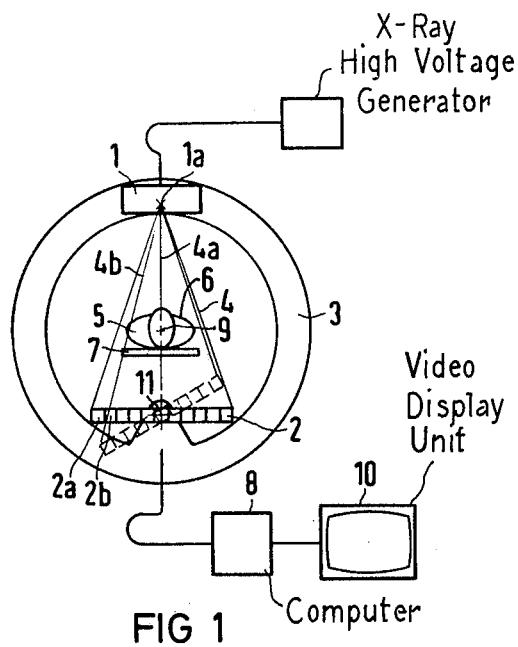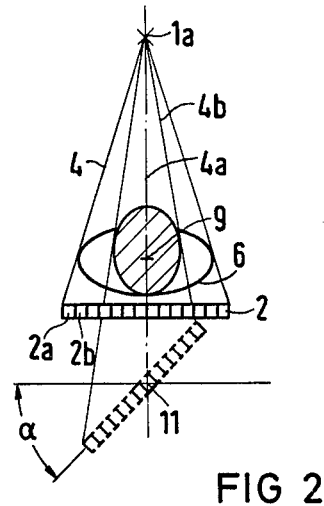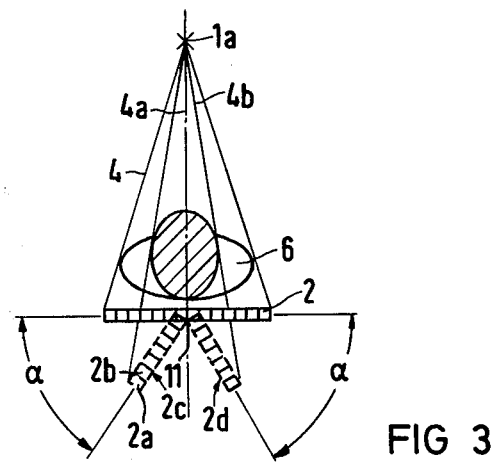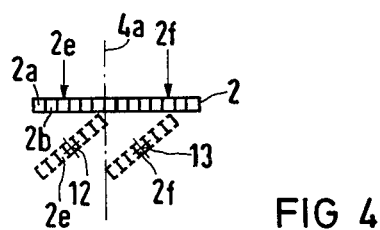

DIAGNOSTIC RADIOLOGY INSTALLATION

BACKGROUND OF THE INVENTION

The invention relates to a diagnostic radiology installation comprising a patient support, a radiation measuring arrangement comprised of a radiation source which generates a fan-shaped radiation beam penetrating the radiography subject and disposed transversely to the patient support, and a radiation receiver which is formed of an array of detectors, means for generating relative movement between the patient support and the radiation measuring arrangement, and a measurand processing circuit for producing an image of the body region scanned during the relative movement.

Diagnostic radiology installations of this type are known in which the measuring arrangement is mounted for rotation about an axis extending parallel to the longitudinal axis of the patient support such that a transverse layer of the patient can be scanned from different projections. Accordingly, the measurand processing circuit then determines an image of the scanned transverse layer. Diagnostic radiology installations of this type are designated as computer tomographs. A computer tomograph of this type is described, for example, in the German OS 27 41 732.

In the case of this known computer tomograph, two radiation receivers, comprised of one detector array, respectively, are provided parallel to one another and adjacent one another, one of which being respectively utilized for the purpose of image-formation. The radiation receivers have different lengths. Given the same number of detectors, a different image resolution thus results in each instance, since the scanned region is smaller in the one case than in the other case. The utilization of two radiation receivers allows the taking into account of the desired image resolution; however, it signifies a considerable outlay.

A diagnostic radiology installation of the type initially cited is also known in which a relative movement between the patient support and the radiation measuring arrangement takes place in a longitudinal direction of the support (German OS 26 13 809). Through this diagnostic radiology installation it is possible to prepare a synoptic radiograph of the body region of the patient scanned during displacement in the longitudinal direction of the support. During this displacement, the measuring arrangement is locked against rotation. In this instance, also, there is the desire to be able to vary the image resolution; i.e., to be able to vary the effective number of detectors per unit of length of a straight line running perpendicularly to the central ray of the radiation beam in the plane of the fan.

SUMMARY OF THE INVENTION

The object underlying the invention resides in designing a diagnostic radiology installation of the type initially cited such that a variation of the image resolution is possible in a simple fashion, without the use of a parallel arrangement of two radiation receivers.

In accordance with the invention, this object is achieved in that the radiation receiver is pivotally mounted about an axis running perpendicular to the fan-plane of the radiation beam. In the case of the inventive diagnostic radiology installation, a simple pivoting of the radiation receivers suffices in order to vary the image resolution.

Another solution of the problem underlying the invention is one wherein the radiation receivers consists of several parts, each of which can be pivoted about an axis running perpendicular to the fan plane of the radiation beam. In this case, only a pivoting of the individual parts of the radiation receiver is necessary for the selection of the image resolution.

The invention shall be explained in greater detail in the following on the basis of several exemplary embodiments illustrated on the accompanying drawing sheet; and other objects, features and advantages will be apparent from this detailed disclosure and from the appended claims.

BRIEF DESCRIPTION OF THE DRAWINGS

FIG. 1 illustrates a diagnostic x-ray installation in accordance with the invention;

FIG. 2 illustrates individual parts of a diagnostic radiology installation in a modification of the embodiment according to FIG. 1; and FIGS. 3 and 4 illustrate variants of the individual parts illustrated in FIG. 2.

DETAILED DESCRIPTION

In FIG. 1, an x-ray tube 1 is illustrated as the radiation source which, with a radiation receiver 2, forms a radiation measuring installation. The radiation receiver 2 exhibits an array of individual detectors 2a, 2b, etc. The x-ray tube 1 is fixedly connected with the radiation receiver 2 via a rotating frame 3, and emits a fan-shaped x-ray beam 4 which permeates a transverse layer 5 of a patient 6 lying on a patient support 7. Perpendicularly to the layer 5 the extent of the x-ray beam 4 corresponds to the layer thickness. The number of detectors 2a, 2b, etc., of the radiation receiver 2 is selected corresponding to the desired image resolution. Every detector delivers a signal which corresponds to the intensity of the received x-radiation.

The detectors 2a, 2b, etc., of the radiation receiver 2 are connected to a computer 8 which, from the output signals of the detectors during the rotation of the measuring arrangement 1, 2, about a rotational axis 9, which runs parallel to the longitudinal direction of the patient support, computes the attenuation values of specific image points of the layer 5, and hence an image of this layer 5 of the patient 6. This image is reproduced on a video display unit 10. Thus, the apparatus illustrated in FIG. 1 represents a computer tomograph in which the layer 5 of the patient 6 is scanned from different projections for the purpose of producing a transverse layer image. The x-ray tube 1 can be pulsed during the scanning operation, so that, for example, in the case of a rotation of 360°, for a complete scanning operation, a set of output signals of the radiation receiver 2 is generated for each angular degree of rotation. In this manner, given 512 detectors in the radiation receiver 2, 360×512 output signals are generated per scan cycle. In the example, for the purpose of clarity, not all detectors are shown, but only a small number are diagrammatically indicated. It is apparent from FIG. 1 that the radiation receiver 2 is pivotally mounted about an axis 11 extending perpendicularly to the fan plane of the radiation beam 4. In FIG. 1, for example, there is illustrated in broken lines a possible position of the radiation receiver 2 which deviates from the position illustrated in solid lines and which is attained by means of pivoting. It is clearly apparent that, during pivoting of the radiation receiver 2 from the illustrated position in which the rectilinear radiation receiver 2 has its optically maximum possible width and is disposed perpendicularly to the central ray 4a of the radiation beam 4, the optical width decreases. In the position illustrated in broken lines, a smaller subject circle is scanned which is determined by the two marginal rays of the radiation beam 4 which are tangents to the latter in every position of the measuring arrangement 1, 2. Since the number of detectors 2a, 2b, etc., in the radiation receiver 2 is always the same, during pivoting of the radiation receiver 2 out of the position illustrated in solid lines, an increase of image resolution accompanied by a reduction of the scanned subject circle results. Thus, through pivoting of the radiation receiver 2 about the axis 11, the image resolution and subject circle can be adapted to the respective requirements.

In FIG. 2, the focus 1a of the x-ray tube 1 and the radiation receiver 2 are illustrated. From FIG. 2 it is apparent that, in the case of this example, the radiation receiver 2, in addition to being mounted pivotally about the axis 11, is also mounted so that the pivot axis can be displaced along the axis of the central ray 4a. This displaceability toward and away from the focus 1a permits an additional influencing of the image resolution.

From FIG. 3 it is apparent that the radiation receiver 2 consists of two parts 2c and 2d which are capable of being folded about the axis 11; namely, in the example, downwardly away from the focus 1a. Thus, the radiation receiver 2 in this example is not, as in the examples according to FIGS. 1 and 2, pivotal as a unit about the axis passing through the center of the radiation receiver 2; on the contrary, it consists of two halves which, at their facing ends, are pivotally mounted about the axis 11. An equidirectional symmetrical pivot movement is thereby possible.

In FIG. 4 it is shown that the radiation receiver 2 consists of two halves 2e and 2f, each of which is pivotally mounted about an axis 12, or 13, respectively, passing through their center and extending perpendicularly to the fan plane of the radiation beam 4. In this instance, it is also possible, in addition to the pivotal movement, to carry out a displacement of the parts 2e and 2f in the direction of the central ray 4a.

In the examples, a collimator is not arranged in front of the radiation receiver 2. If a collimator is provided, precaution must be exercised to ensure that its leaves remain aligned (or orientated) to the focus 1a even during pivoting of the radiation receiver 2.

The illustrated embodiments are suitable for the preparation of computer tomograms through rotation of the measuring arrangement 1, 2, about the axis 9, as well as for the preparation of synoptic radiographs with the aid of a relative movement between the measuring arrangement 1, 2, which is locked against rotation, and the patient support 7, through a predetermined range and they permit, in both instances, the adaptation of the image resolution and of the scanned field to the respective requirements.

It is also possible, in the case of a radiation receiver designed as a unit, to place the pivot axis at one end of the radiation receiver.

In the example according to FIG. 4, through a corresponding movement of the parts 2e and 2f of the radiation receiver 2 in a direction toward one another or away from one another, it must be ensured that no gap for the radiation results between the two parts 2e and 2f during pivoting.

In order to avoid a cross-talk type of interference, the detectors 2a, 2b, etc., can be separated from one another by means of radiation-absorbing walls.

The varying focus-detector-intervals resulting during tilting of the radiation receiver 2 can be taken into account by way of computation (in the computer 8).

It will be apparent that many modifications and variations may be effected without departing from the scope of the novel concepts and teachings of the present invention.

I claim as my invention:

1. A diagnostic radiology installation comprising a patient support, a radiation measuring arrangement comprised of a radiation source, which generates a fan-shaped radiation beam lying in a fan-plane and penetrating the radiography subject, and of a radiation receiver having an array of detectors, means for producing a relative movement between the patient support and the radiation measuring arrangement, and a measurand processing circuit for the formation of an image of the body region scanned during the relative movement, the improvement comprising said radiation receiver being pivotally mounted for pivotal movement about a pivot axis extending perpendicularly to the fan-plane of the radiation beam, said radiation receiver being pivotally movable relative to the radiation beam so as to adjust the resolution of the radiation receiver.

2. A diagnostic radiology installation according to claim 1, with said radiation receiver being pivotally mounted such that the pivot axis extends through the center of the radiation receiver.

3. A diagnostic radiology installation according to claim 2, with the radiation receiver being pivotal as a unit about the pivot axis.

4. A diagnostic radiology installation according to claim 2, with the radiation receiver comprising two halves which, at their mutually facing ends, are pivotally mounted about the pivot axis.

5. A diagnostic radiology installation comprising a patient support, a radiation measuring arrangement comprised of a radiation source which generates a fan-shaped radiation beam penetrating the radiography subject, and a radiation receiver having an array of detectors, means for producing a relative movement between the patient support and the radiation measuring arrangement, and a measurand processing circuit for the formation of an image of the body region scanned during the relative movement, the improvement comprising the radiation receiver having a plurality of parts, each of which is pivotally mounted about an individual pivot axis disposed perpendicularly to the fan-plane of the radiation beam, the individual pivot axes of the respective parts being offset from each other, and the respective parts of the radiation receiver being pivotally movable relative to respective portions of the radiation beam so as to adjust the resolution of the respective parts of the radiation receiver.

* * * * *